(12) United States Patent
Askarinya et al.

(10) Patent No.: US 9,496,241 B2
(45) Date of Patent: Nov. 15, 2016

(54) INTEGRATED CIRCUIT PACKAGING FOR IMPLANTABLE MEDICAL DEVICES

(71) Applicant: Medtronic, Inc., Minneapolis, MN (US)

(72) Inventors: Mohsen Askarinya, Chandler, AZ (US); Mark R Boone, Gilbert, AZ (US); Andreas A Fenner, Chandler, AZ (US); Lejun Wang, San Diego, CA (US); Kenneth Heames, Mesa, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/473,156

(22) Filed: Aug. 29, 2014

(65) Prior Publication Data
US 2014/0368266 A1  Dec. 18, 2014

Related U.S. Application Data

(62) Division of application No. 13/524,368, filed on Jun. 15, 2012, now Pat. No. 8,824,161.

(51) Int. Cl.
*H05K 1/18* (2006.01)
*H01L 25/00* (2006.01)
(Continued)

(52) U.S. Cl.
CPC ............. *H01L 25/00* (2013.01); *A61N 1/3758* (2013.01); *A61N 1/3968* (2013.01);
(Continued)

(58) Field of Classification Search
CPC ............ H05K 1/16; H05K 3/28; H05K 7/00; H05K 7/20; H01F 17/00; H01F 17/0013; H01F 27/28; H01F 27/34; H01F 30/10; H01L 21/33; G05F 1/325; G05F 3/06; G01D 5/12

USPC ....... 361/764, 270, 707, 723, 728, 748, 765, 361/782, 785, 793; 336/83, 181, 200, 229, 336/232; 333/25, 131, 177; 363/17, 19, 59, 363/131, 144; 323/250; 438/138; 257/446; 71/866.1

See application file for complete search history.

(56) References Cited

U.S. PATENT DOCUMENTS 4,730,241 A * 3/1988 Takaya ............................ 363/19
4,780,795 A * 10/1988 Meinel ........................... 361/765
(Continued)

FOREIGN PATENT DOCUMENTS

CN 1396641 A 2/2003
EP 2 107 599 A2 10/2009
(Continued)

OTHER PUBLICATIONS

Boone, "Planar Transformer Assemblies for Implantable Cardioverter Defibrillators", filed Jun. 15, 2012, U.S. Appl. No. 13/524,222, 13 pages.
(Continued)

*Primary Examiner* — Xiaoliang Chen
(74) *Attorney, Agent, or Firm* — Evans M. Mburu

(57) ABSTRACT

A hybrid integrated circuit in a wafer level package for an implantable medical device includes one or more passive component windings formed, at least in part, along one or more routing layers of the package. The windings may be primary and secondary windings of a transformer, wherein all or part of a magnetic core thereof is embedded in a component layer of the wafer level package. If the core includes a part bonded to a surface of the package, that part of the core may be E-shaped with legs extending into the routing layers, and, in some cases, through the routing layers. Routing layers may be formed on both sides of the component layer to accommodate the transformer windings, in some instances.

10 Claims, 8 Drawing Sheets

(51) Int. Cl.
*H01F 27/28* (2006.01)
*H01L 23/64* (2006.01)
*H01L 25/16* (2006.01)
*A61N 1/375* (2006.01)
*A61N 1/39* (2006.01)

(52) U.S. Cl.
CPC ....... *H01F 27/2804* (2013.01); *H01L 23/647* (2013.01); *H01L 25/16* (2013.01); *H01F 2027/2819* (2013.01); *H01L 2924/0002* (2013.01)

(56) References Cited

U.S. PATENT DOCUMENTS

| | | | |
|---|---|---|---|
| 5,191,517 A * | 3/1993 | Stephenson | 363/59 |
| 5,434,493 A | 7/1995 | Woody et al. | |
| 5,515,259 A * | 5/1996 | Stephenson | 363/59 |
| 5,523,939 A * | 6/1996 | Stephenson | 363/59 |
| 5,583,474 A * | 12/1996 | Mizoguchi et al. | 336/83 |
| 5,598,327 A * | 1/1997 | Somerville et al. | 363/131 |
| 5,615,091 A * | 3/1997 | Palatnik | 363/17 |
| 5,631,822 A * | 5/1997 | Silberkleit et al. | 363/144 |
| 5,863,806 A | 1/1999 | Lue | |
| 6,087,922 A | 7/2000 | Smith | |
| 6,094,597 A | 7/2000 | Wold | |
| 6,124,778 A * | 9/2000 | Rowley et al. | 336/200 |
| 6,222,437 B1 | 4/2001 | Soto et al. | |
| 6,233,834 B1 | 5/2001 | Walsh | |
| 6,278,354 B1 | 8/2001 | Booth | |
| 6,369,685 B1 * | 4/2002 | Milavec et al. | 336/232 |
| 6,392,525 B1 | 5/2002 | Kato et al. | |
| 6,420,953 B1 | 7/2002 | Dadafshar | |
| 6,476,704 B2 | 11/2002 | Goff | |
| 6,477,414 B1 | 11/2002 | Silvian | |
| 6,716,672 B2 | 4/2004 | Val | |
| 6,782,290 B2 | 8/2004 | Schmidt | |
| 6,927,663 B2 | 8/2005 | Iverson et al. | |
| 6,980,074 B1 * | 12/2005 | Jitaru | 336/200 |
| 7,120,492 B2 | 10/2006 | Iverson et al. | |
| 7,167,074 B2 | 1/2007 | Fenner et al. | |
| 7,180,397 B1 * | 2/2007 | Busletta et al. | 336/200 |
| 7,225,018 B2 | 5/2007 | Iverson et al. | |
| 7,292,126 B2 | 11/2007 | So | |
| 7,351,593 B1 | 4/2008 | Johnson et al. | |
| 7,375,609 B2 | 5/2008 | Suzuki et al. | |
| 7,436,683 B2 | 10/2008 | Shen | |
| 7,463,131 B1 | 12/2008 | Hwang et al. | |
| 7,476,965 B2 | 1/2009 | Val et al. | |
| 7,489,226 B1 * | 2/2009 | Chignola et al. | 336/229 |
| 7,541,662 B2 | 6/2009 | Sim et al. | |
| 7,635,639 B2 | 12/2009 | Val et al. | |
| 7,652,348 B1 | 1/2010 | Hopper et al. | |
| 7,671,714 B2 | 3/2010 | Tiemeijer | |
| 7,829,425 B1 | 11/2010 | Hopper et al. | |
| 7,847,669 B2 | 12/2010 | Ayazi et al. | |
| 7,852,635 B1 * | 12/2010 | Busletta et al. | 361/784 |
| 7,877,874 B2 | 2/2011 | Val | |
| 8,824,161 B2 | 9/2014 | Askarinya et al. | |
| 8,830,693 B2 | 9/2014 | Boone | |
| 2001/0024838 A1 | 9/2001 | Ma | |
| 2002/0030961 A1 * | 3/2002 | Waffenschmidt et al. | 361/270 |
| 2002/0070835 A1 | 6/2002 | Dadafshar | |
| 2002/0075116 A1 * | 6/2002 | Peels et al. | 336/200 |
| 2002/0135076 A1 | 9/2002 | Huang et al. | |
| 2002/0139990 A1 | 10/2002 | Suehiro et al. | |
| 2002/0161404 A1 | 10/2002 | Schmidt | |
| 2002/0185726 A1 | 12/2002 | North et al. | |
| 2004/0001021 A1 | 1/2004 | Choo et al. | |
| 2004/0110323 A1 | 6/2004 | Becker et al. | |
| 2004/0258984 A1 | 12/2004 | Ariel et al. | |
| 2005/0017054 A1 | 1/2005 | Iverson et al. | |
| 2005/0024838 A1 * | 2/2005 | Maxwell | 361/782 |
| 2005/0107870 A1 | 5/2005 | Wang et al. | |
| 2005/0212618 A1 * | 9/2005 | Setty et al. | 333/131 |
| 2005/0230837 A1 | 10/2005 | Taghizadeh-Kaschani | |
| 2005/0258925 A1 | 11/2005 | Iverson et al. | |
| 2005/0269657 A1 * | 12/2005 | Dupuis | 257/446 |
| 2005/0270745 A1 * | 12/2005 | Chen et al. | 361/707 |
| 2005/0270806 A1 * | 12/2005 | Zhu | 363/17 |
| 2006/0038549 A1 * | 2/2006 | Mehrotra et al. | 323/306 |
| 2006/0111752 A1 | 5/2006 | Greatbatch et al. | |
| 2006/0129192 A1 | 6/2006 | Greatbatch et al. | |
| 2006/0284717 A1 | 12/2006 | Iverson et al. | |
| 2007/0030659 A1 * | 2/2007 | Suzuki et al. | 361/793 |
| 2007/0132079 A1 | 6/2007 | Otremba et al. | |
| 2007/0216377 A1 * | 9/2007 | Yoshimura | 323/250 |
| 2007/0218595 A1 * | 9/2007 | Yoshimura | 438/138 |
| 2007/0251339 A1 * | 11/2007 | Wiese et al. | 73/866.1 |
| 2007/0296533 A1 * | 12/2007 | Springett | 336/200 |
| 2008/0061631 A1 * | 3/2008 | Fouquet et al. | 307/109 |
| 2008/0094164 A1 | 4/2008 | Hsu | |
| 2008/0266042 A1 * | 10/2008 | Yoshimura et al. | 336/181 |
| 2009/0093772 A1 | 4/2009 | Genosar et al. | |
| 2009/0102038 A1 | 4/2009 | Mcelrea et al. | |
| 2009/0261468 A1 | 10/2009 | Kroeninger et al. | |
| 2009/0306594 A1 | 12/2009 | Pang et al. | |
| 2009/0318102 A1 | 12/2009 | Someya | |
| 2010/0012101 A1 | 1/2010 | Fujinuma et al. | |
| 2010/0013101 A1 | 1/2010 | Hedler et al. | |
| 2010/0052839 A1 * | 3/2010 | Mertens et al. | 336/232 |
| 2010/0087778 A1 | 4/2010 | Genosar et al. | |
| 2010/0091464 A1 * | 4/2010 | Ohnishi et al. | 361/723 |
| 2010/0140791 A1 | 6/2010 | Chen | |
| 2010/0148910 A1 | 6/2010 | Takada | |
| 2010/0312310 A1 | 12/2010 | Meskens | |
| 2011/0037405 A1 * | 2/2011 | Suganuma et al. | 315/276 |
| 2011/0084607 A1 * | 4/2011 | Hopper et al. | 315/53 |
| 2012/0146741 A1 * | 6/2012 | Yen et al. | 333/25 |
| 2012/0287582 A1 * | 11/2012 | Vinciarelli et al. | 361/728 |
| 2013/0257564 A1 * | 10/2013 | Huang et al. | 333/177 |
| 2013/0335927 A1 | 12/2013 | Boone | |
| 2014/0355218 A1 * | 12/2014 | Vinciarelli et al. | 361/728 |

FOREIGN PATENT DOCUMENTS

| | | | |
|---|---|---|---|
| WO | 02/095775 | A1 | 11/2002 |
| WO | 2008008587 | A2 | 1/2008 |
| WO | 2010019485 | A2 | 2/2010 |

OTHER PUBLICATIONS

Boone, et al., "Wafer Level Packages of High Voltage Units for Implantable Medical Devices and Corresponding Fabrication Methods", filed Jun. 15, 2012, U.S. Appl. No. 13/524,253, 29 pages.

Askarinya et al., "Power Sources Suitable for Use in Implantable Medical Devices and Corresponding Fabrication Methods", filed Jun. 15, 2012, U.S. Appl. No. 13/524,304, 15 pages.

Wafer Level Stack—WDoD™—Reliable Miniaturization Technologies for Electronics located on-line at http://www.3d-plus.com/techno-wafer-level-stack-wdod.php.

Kwoka et al., Intersil Technical Brief, PCB Land Pattern Design and Surface Mount Guidelines for QFN Packages, Apr. 23, 2009, TB389.6, 9 pages—also located on-line at http://www.intersil.com/data/tb/TB389.pdf.

Meyer et al., "System-Integration with eWLB", Electronic System-Integration Technology Conference, 2010, Sep. 13, 2010, 10 pages.

Yonggang et al., "Next Generation eWLB (Embedded Wafer Level BGA) Packaging", 2010 12th Electronics Packaging Technology Conference, Dec. 1, 2010, 8 pages.

(PCT/US2013/035056) PCT Notification of Transmittal of the International Search Report and the Written Opinion of the International Searching Authority, Jul. 1, 2013, 13 pages.

Chinese Office Action, Application No. 2013800311663, Nov. 11, 2015, English Translation, 10 pages.

Chinese Office Action, Application No. 2013800311663, Nov. 11, 2015, 7 pages.

\* cited by examiner

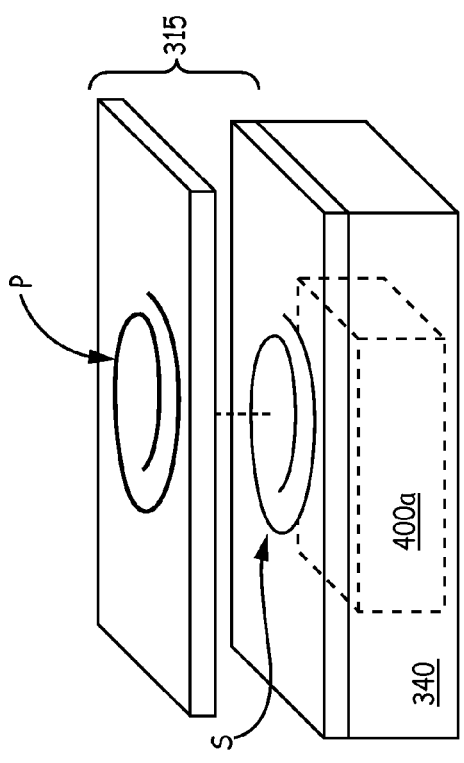
FIG. 4A
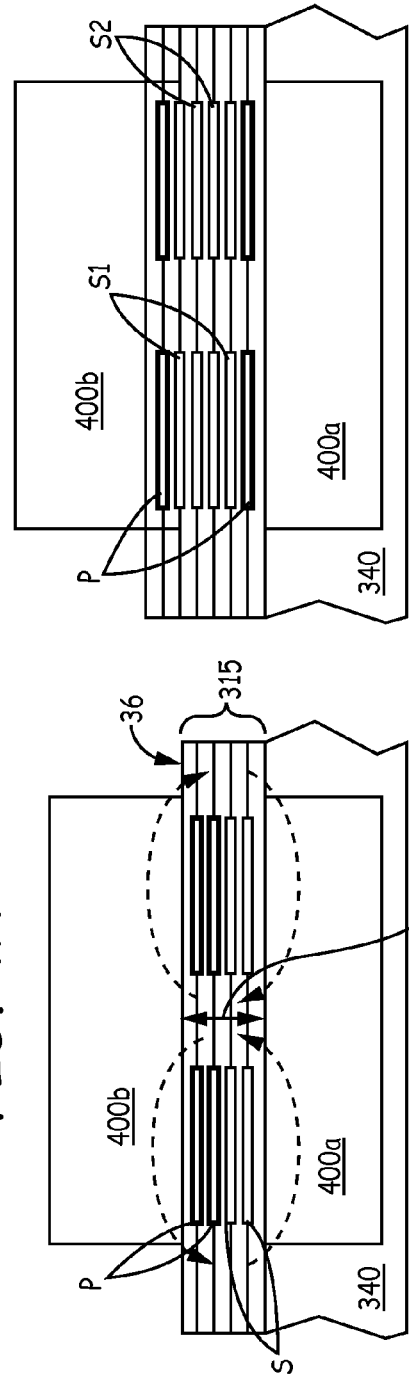
FIG. 4B
FIG. 4C

INTEGRATED CIRCUIT PACKAGING FOR IMPLANTABLE MEDICAL DEVICES

CROSS-REFERENCE TO RELATED APPLICATION

The present application is a divisional of U.S. patent application Ser. No. 13/524,368, which is entitled INTEGRATED CIRCUIT PACKAGING FOR IMPLANTABLE MEDICAL DEVICES, filed on Jun. 15, 2012.

FIELD OF THE DISCLOSURE

The present invention pertains to integrated circuit packaging, and, more specifically, to wafer level packages for implantable medical devices (IMD's).

BACKGROUND

The packaging of hybrid integrated circuits continues to evolve in response to downsizing demands common among a number of industries. Those skilled in the art are familiar with redistributed chip packaging (RCP) processes employed in conjunction with artificial, or reconstituted wafers, to form hybrid integrated circuits in relatively thin (planar) wafer level packages. In the medical device industry, the construction of IMD's can benefit from such electronics packaging.

FIG. 1 is a schematic showing a typical IMD 100, which is suitable for cardiac monitoring and/or therapy delivery, implanted at a subcutaneous pectoral site in a patient 102. FIG. 1 illustrates IMD 100 including a hermetically sealed and biocompatible canister 104, for example, formed from a Titanium alloy, which houses a power source and electronic circuitry, and one or more electrical leads 106, which are coupled to the circuitry and extend distally from canister 104, through the venous system 110 and into the heart 108 of patient 102, for example, the right ventricle (RV). Those skilled in the art understand that the one or more leads 106 preferably include sensing and therapy delivery electrodes, which are coupled to the IMD circuitry via one or more lead connectors that terminate elongate insulated conductors of the electrodes, at a proximal end of lead(s) 106; the one or more lead connectors are plugged into a connector module 105, which is mounted on canister 104, to make electrical contact with the contained IMD circuitry via hermetically sealed feedthroughs.

IMD 100 may function as an implantable cardioverter defibrillator (ICD) to detect atrial and/or ventricular fibrillation and, in response to the detection, to deliver high voltage shock therapy in order to terminate the fibrillation. FIG. 2 is a simplified circuit diagram for an exemplary voltage generator portion of ICD circuitry. FIG. 2 illustrates a flyback transformer 240 connected across terminals of a power source 220, a switch 232 connected in series with a primary winding of transformer 240, and a diode 234 connected in series with a secondary winding of transformer 240 across a load, which includes a capacitor element 239 connected by another switch 236 to heart 108, for example, via one or more leads 106 (FIG. 1). FIG. 2 further illustrates a sense circuit 260 that monitors voltage of capacitor element 239, and a controller 210 that receives a signal from the sense circuit 260 to deliver energy from power source 220 when the voltage of capacitor element 239 is below a predetermined threshold. Those skilled in the art will appreciate that a cycling of switch 232 causes transformer 240 to incrementally charge capacitor element 239 to generate voltage on the order of 750 volts or more, so that, when switch 236 is closed, defibrillation shock energy, for example, at a level in the range of 5-40 Joules may be delivered to heart 108.

In the past, transformer 240 would be constructed as a conventional type of flyback transformer from components that are physically separate from one another and from other electrical components of the ICD circuitry, for example, primary and secondary windings formed around a toroid-shaped magnetic core. Because these components of the conventional transformer take up a relatively large amount of space within canister 104, recent efforts to reduce an overall size of canister 104, for a more comfortable implant, have focused on reducing the size of flyback transformers that are employed for charging ICD capacitors. Commonly-assigned U.S. Pat. No. 7,167,074 describes the construction of planar flyback transformers, for physical integration of the transformer with other elements of ICD circuitry, wherein primary and secondary windings are embedded between opposing sides of a printed circuit board (PCB) to which a planar magnetic core is mounted (i.e. E-shaped core with legs/feet extending through openings in the PCB such that the windings are disposed thereabout). Although the embodiments of planar flyback transformers that are described in the '074 Patent can reduce the amount of space taken up by a transformer, such as transformer 240 within canister 104, there is still a need for improved assemblies of planar flyback transformers, as well as other passive components that include windings (i.e. antennas for telemetry modules), which can be integrated into wafer level packages of hybrid integrated circuits, for further downsizing of IMD's.

SUMMARY

A hybrid integrated circuit formed in a wafer level package for an implantable medical device, according to embodiments of the present invention, is fabricated according to reconstituted wafer and RCP processes, and includes one or more passive component windings formed, at least in part, along one or more of the plurality of redistribution, or routing layers. According to some preferred embodiments, the windings are primary and secondary windings of a transformer, wherein a first part of a planar magnetic core thereof is embedded in the artificial wafer, or component layer of the wafer level package, and a second part of the core is bonded to a surface of the package that overlays the plurality of routing layers. The primary and secondary windings of the transformer may be formed in a planar spiral configuration, wherein each winding may be formed on more than one routing layer; alternately the windings may be formed in a planar helical configuration with turns spanning multiple routing layers. According to some embodiments, a thickness of the plurality of routing layers defines a core gap of the transformer, while, according to some alternate embodiments, the second part of the magnetic core includes three legs spaced apart from one another (i.e. E-shaped) to minimize the core gap; the legs extend from the surface of the package that overlays the plurality of routing layers, and either into the plurality of routing layers, for example, such that the core gap spans a thickness of approximately one routing layer, or through the plurality of routing layers and into close proximity with the first part of the magnetic core.

In some transformer embodiments, routing layers are formed on opposing sides of the component layer. According to some of these embodiments, the opposing routing layers provide additional substrates on which windings may be formed (—to increase a number of winding turns and/or a number of secondary windings), in which case the magnetic core includes two E-shaped parts, which are bonded to opposing surfaces of the package with legs extending from the respective surface and through the corresponding routing layers, and the part of the core that is embedded within the routing layer is divided into three columns that effectively extend the legs of one of the E-shaped parts of the core. According to some alternate embodiments, the transformer includes a toroid-shaped planar magnetic core that is embedded within the component layer and, preferably, spans a thickness thereof. Primary and secondary windings of these transformers that include the planar toroid-shaped core have inner and outer portions and top and bottom portions; the inner and outer portions extend through a thickness of the component layer, inside and outside, respectively, of a perimeter of the magnetic core, and the top and bottom portions extend along first and second routing layers, respectively, on opposite sides of the component layer, wherein each of the top and bottom portions connect an inner portion to a corresponding outer portion.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIGS. 4A-B are an exploded schematic and a cross-section view, each of a portion of a wafer level package, according to some embodiments of the present invention;

FIG. 4C is a cross-section view of a portion of a wafer level package, according to some alternate embodiments;

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
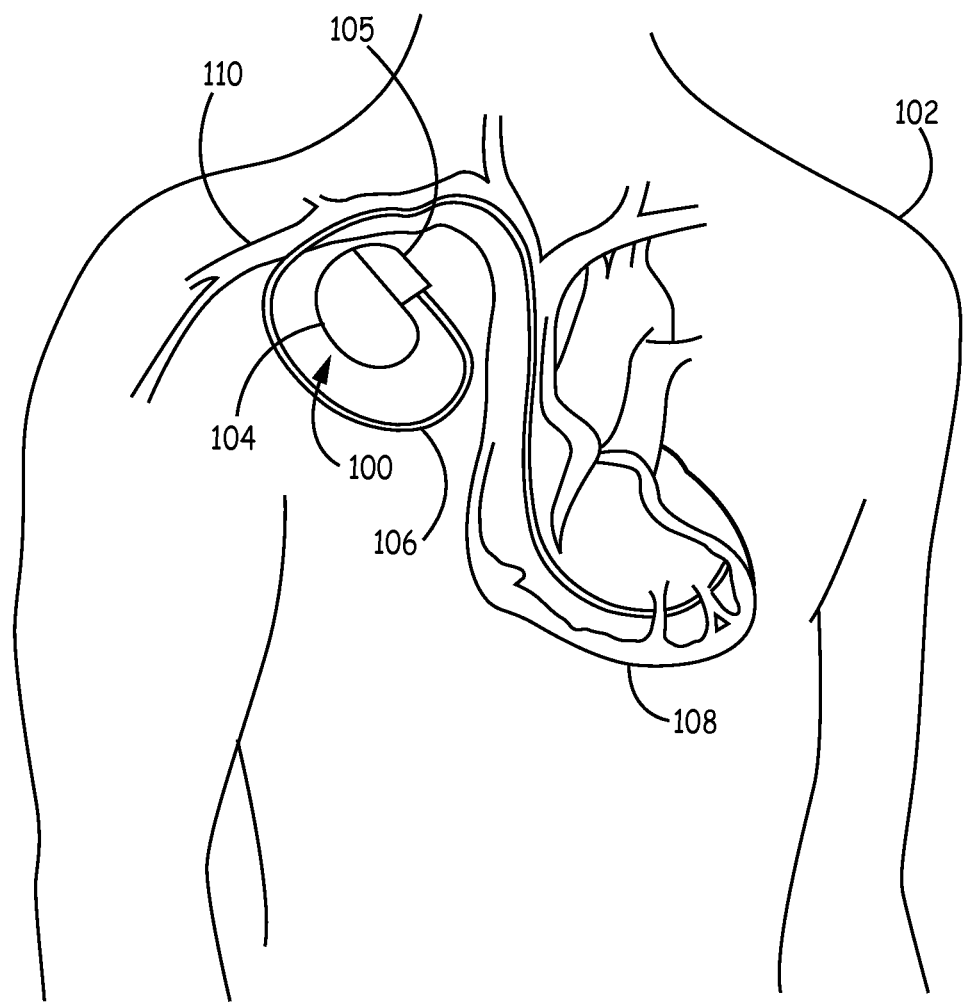
FIG. 1 is a schematic showing a typical placement of an implanted medical device.
Figure 2:
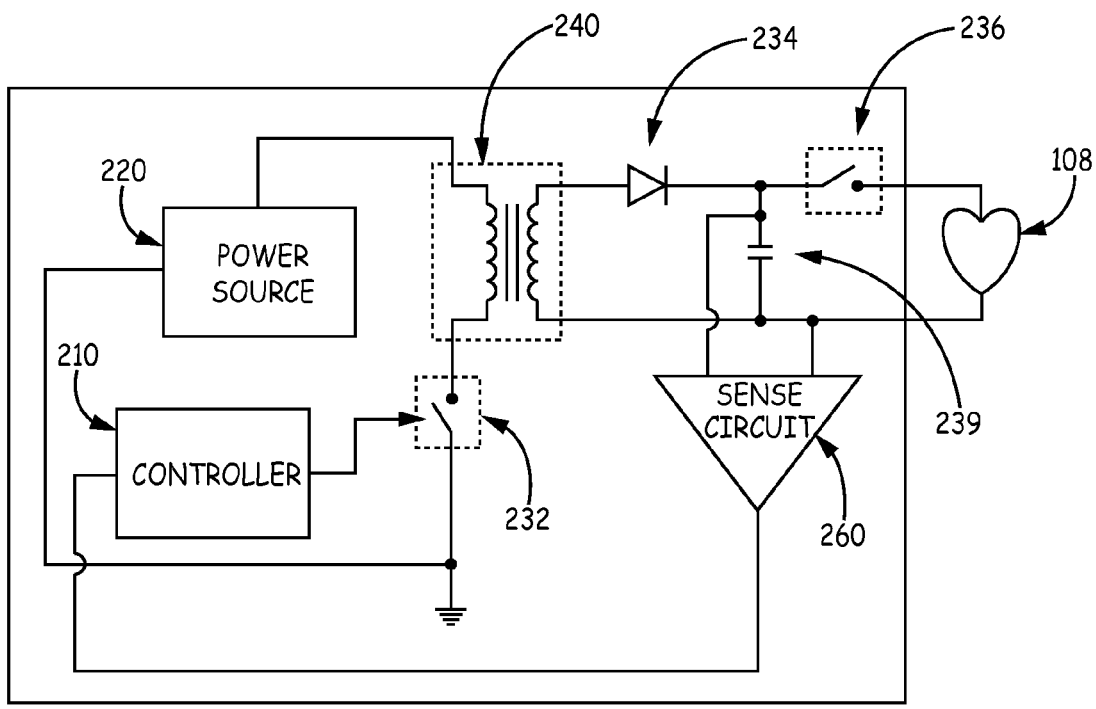
FIG. 2 is a simplified circuit diagram of circuitry that may be employed by the device shown in FIG. 1.
Figure 3A:
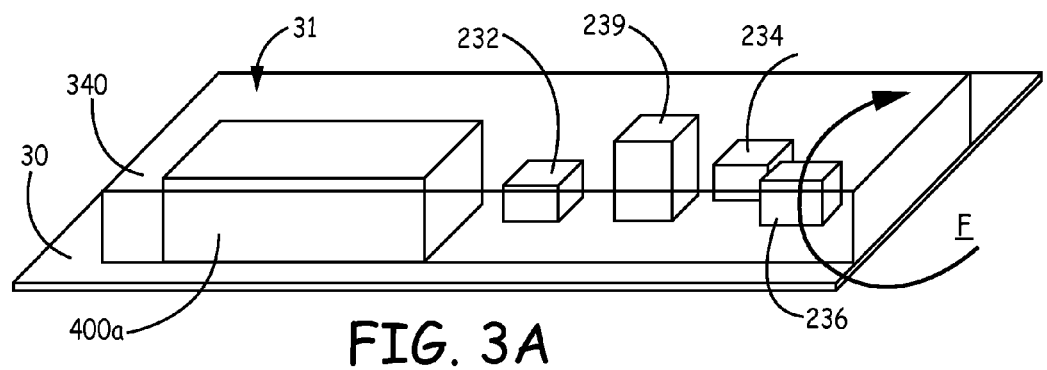
FIG. 3A is a schematic showing an assembly of one or more active devices and passive components, along with a portion of a transformer core, within an artificial/reconstituted wafer, according to some embodiments of the present invention.

FIG. 3A is a schematic showing one or more passive components and active devices, for example, capacitor element 239, and switches 232, 236 and diode 234, respectively, of the ICD circuitry of FIG. 2 (described above), having been assembled together, along with a first part 400a of a magnetic core of a transformer, for example, transformer 240 of FIG. 2, on a flat tape substrate 30 that serves as temporary support. FIG. 3A illustrates core part 400a and devices/components 232, 236, 234 encapsulated together within in a polymer mold compound (i.e. an epoxy based thermoset including a non-conductive filler such as $AlO_2$ or $SiO_2$, about 80% by volume) to form an artificial/reconstituted wafer, or component layer 340 of a wafer level package WLP, which is shown in the exploded schematic of FIG. 3B. According to the illustrated embodiment, after the mold compound cures, component layer 340 is flipped, per arrow F, so that a side 31 of component layer 340 faces downward, and tape 30 is removed, prior to performing an RCP process to successively build up each dielectric (i.e. epoxy or polyimide or benzocyclobutene polymer) and corresponding trace(s), or conductive runners (i.e. copper) of a plurality of redistribution, or routing layers 315, on an opposite side 32 of component layer 340, according to fabrication methods known in the art. According to exemplary embodiments, a thickness of component layer 340 may be between approximately 300 micrometers and approximately 1100 micrometers, and a thickness of each routing layer may be between approximately 12 micrometers and approximately 25 micrometers.

Figure 3B:
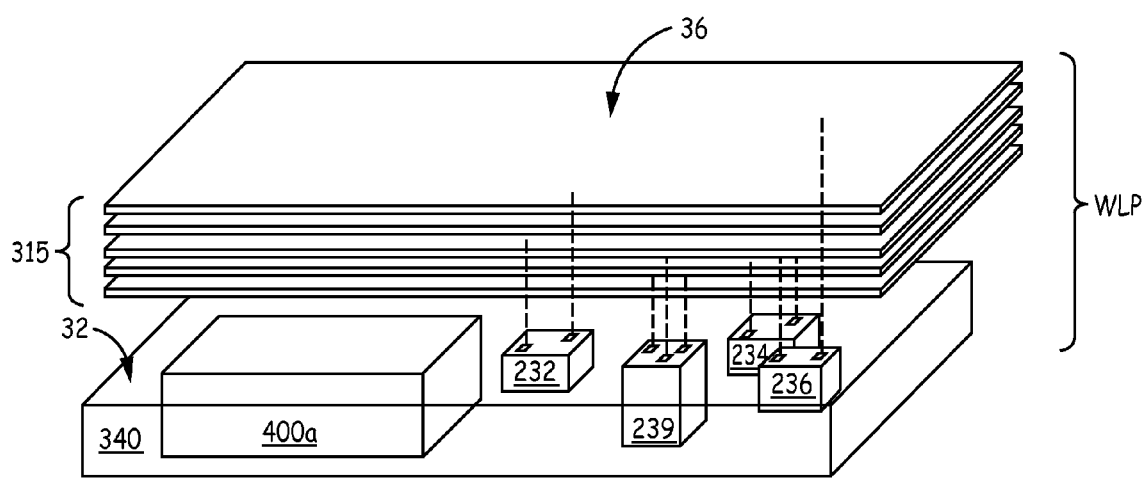
FIG. 3B is an exploded schematic of a wafer level package including the reconstituted wafer of FIG. 3A, according to some embodiments.
Figure 5A:
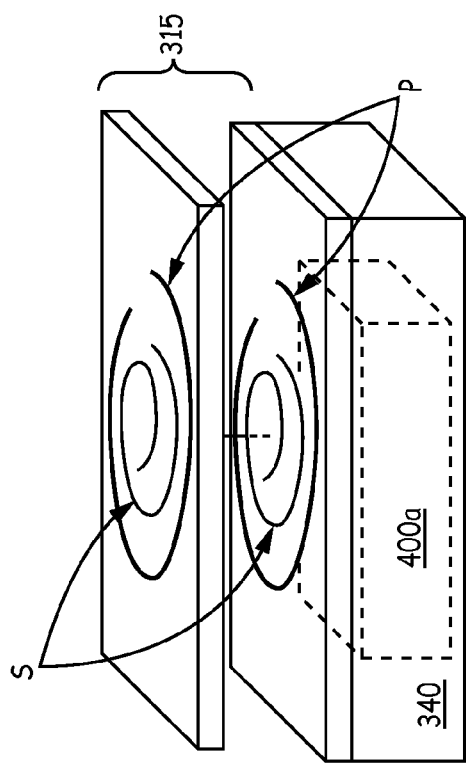
FIGS. 5A-B are an exploded schematic and a cross-section view, each of a portion of a wafer level package, according to some additional embodiments of the present invention.
Figure 7:
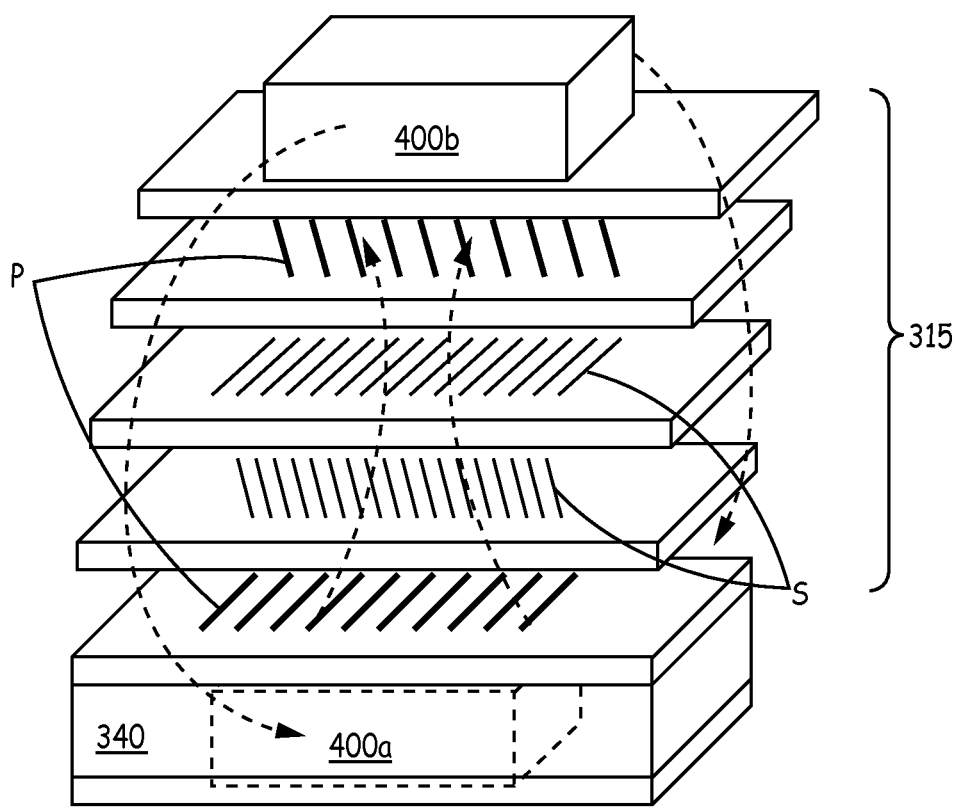
FIG. 7 is an exploded view of a portion of a wafer level package according to further embodiments.

The dashed lines in FIG. 3B represent exemplary vias extending from electrical contacts of each device/component 232, 234, 236, 239 through one or more corresponding layers of the plurality of routing layers 315; each via extends to a corresponding conductive runner (not shown) within the routing layers to make the appropriate electrical couplings among the embedded components, or to bond pads (not shown) at a surface 36 of wafer level package WLP. According to some preferred embodiments of the present invention, primary and secondary windings of a transformer, for example, transformer 240, are also formed by conductive traces in routing layers 315, wherein the terminal ends thereof are coupled, within the routing layers 315, to conductive runners of the corresponding device/component of component layer 340. It should be noted that other passive components that are in the form of windings, such as inductors and antennas, may also be formed by conductive traces in routing layers 315; for example, an antenna formed in routing layers 315 may be coupled to a telemetry module embedded in component layer 340. The windings may be formed in a planar spiral configuration, for example, as illustrated in FIGS. 4A and 5A, wherein the winding turns extend around an axis that is approximately orthogonal to the major plane of each routing layer; or the windings may be formed in a cross-planar helical configuration, for example, as illustrated in FIG. 7, wherein the winding turns extend around an axis that is approximately parallel to the major plane of each routing layer.

Figure 5C:
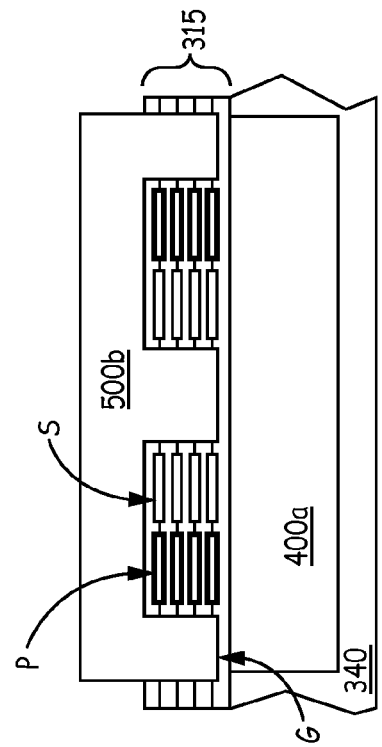
FIGS. 5C and 6 are cross-section views of portions of a wafer level package, according to some other alternate embodiments.
Figure 5B:
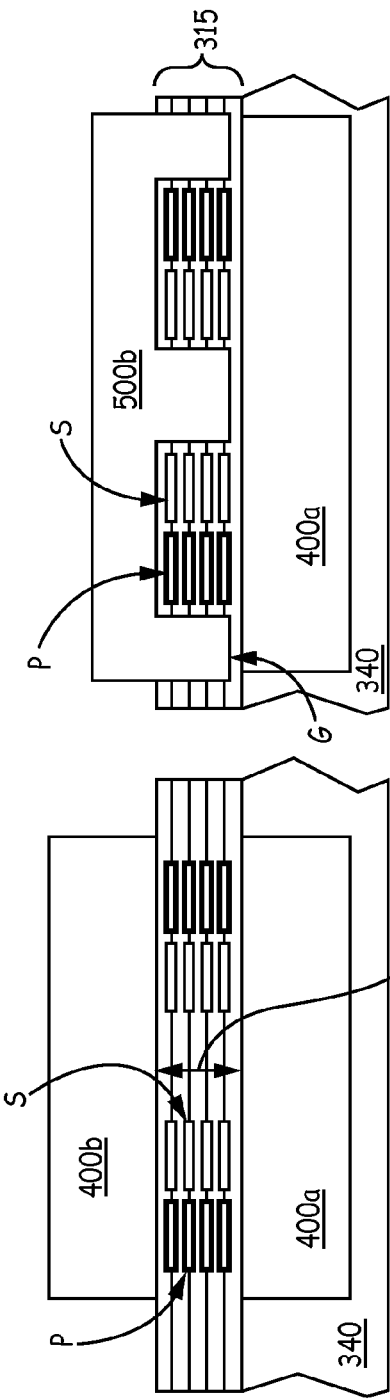

FIG. 4A is an exploded schematic of a portion of wafer level package WLP that illustrates a primary transformer winding P and one or more secondary transformer windings S, each formed in a planar spiral configuration on a separate routing layer of the plurality of routing layers 315, according to some embodiments. For the purpose of clarity in illustration, all of routing layers are not shown and the dotted line is used to designate intermediate routing layers which are not shown. FIG. 4B is a cross-section view of the portion of the same wafer level package WLP, which shows primary winding P formed on two layers of the plurality of routing layers 315, wherein vias (not shown) extend between respective routing layers to electrically couple the parts of primary winding. Secondary windings S may also be formed on at least two layers of the plurality of routing layers 315, as illustrated, or two secondary windings, one formed on each layer, may be employed. FIGS. 5A-B illustrate an alternate arrangement of transformer windings wherein turns of secondary winding(s) S are formed on the same layers as turns of primary winding P.

FIGS. 4B and 5B further illustrates a second part 400b of the magnetic core bonded, for example, by a relatively thin adhesive layer (i.e. non-conductive epoxy or pressure sensitive adhesive), to solder mask surface 36 of wafer level package WLP that overlays routing layers 315. The magnetic core may be formed from any of a variety of soft ferrite materials known in the art, and each part 400a, 400b of the core may have a thickness of between approximately 350 micrometers and approximately 1100 micrometers. With further reference to FIG. 4B, dashed line arrows illustrate the magnetic flux path of the core. According to some alternate embodiments, which are described in greater detail below, the magnetic core is formed from a distributed gap material, such as Molybdenum permalloy powder (MPP).

According to some preferred embodiments, capacitor element 239 includes a plurality of storage capacitors stacked in series, so the transformer includes a corresponding plurality of secondary windings, one for each capacitor, each of which may be formed on a single layer of routing layers 315, or, preferably, on more than one of routing layers 315, for example, as illustrated in the cross-section of FIG. 4C. FIG. 4C shows secondary windings S1, S2 arranged in a nested fashion, such that a first pair of routing layers, on which a first secondary winding S1 is formed, is located in between individual routing layers of a second pair of routing layers on which a second secondary winding S2 is formed. FIG. 4C further illustrates primary winding P formed on a pair of routing layers between which secondary windings S1, S2 are sandwiched. Secondary windings S1, S2 are preferably arranged in a hierarchical fashion (i.e. a DC voltage, with respect to ground, of second secondary winding S2 is lower than that of first secondary winding S1, with respect to ground) in order to minimize electric field, for example, as described in the above-referenced related U.S. patent application Ser. No. 13/524,222. The illustrated arrangement of transformer windings and suitable alternate arrangements that may be employed in embodiments of the present invention, are described in the above-referenced related U.S. patent application Ser. No. 13/524,222, which is hereby incorporated by reference in its entirety.

With further reference to FIGS. 4A-B and 5A-B, it may be appreciated that a gap G between first and second parts 400a, 400b of the magnetic core is dictated by the number of intervening routing layers 315, which, in turn, may be dictated by the configuration of the transformer windings. For those embodiments that employ ferrite magnetic cores, the required gap G is typically between approximately 25 micrometers and approximately 150 micrometers. According to an exemplary embodiment, a thickness of each routing layer is between approximately 12 micrometers and approximately 25 micrometers. In order to reduce gap G, part of the magnetic core may be E-shaped with legs extending into routing layers 315 like a part 500b illustrated in FIGS. 5C and 6. With reference to FIG. 5C, openings to receive the legs of magnetic core part 500b, for example, having a maximum cross-sectional dimension on the order of 1 mm to 10 mm, may be formed through the dielectric material of routing layers 315 (between the various conductive runners), for example, by laser or mechanical milling, and part 500b may be bonded to surface 36, similar to part 400b. It should be noted that part 500b may be substituted for part 400b in the embodiments of FIGS. 4A-C, according to some alternate embodiments. If the magnetic core is formed from a distributed gap material, such as the aforementioned MPP, rather than from a ferrite material, a relatively small gap, for example, less than 25 micrometers, is desired for higher inductance, and intimate contact between core parts is preferred. In this case, the legs of part 500b extend all the way through routing layers 315, and are either in intimate contact with part 400a, or are separated from part 400a by only a thickness of an adhesive layer, that may be employed to anchor the legs within the openings.

Figure 6:
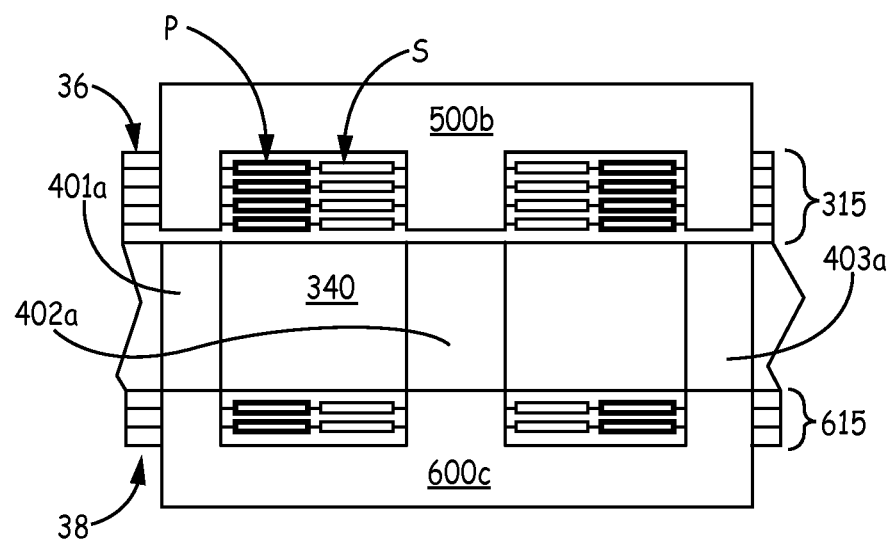

Turning now to FIG. 6, according to some embodiments, wafer level package WLP includes another plurality of routing layers 615 formed on side 31 (FIG. 3A) of component layer 340, opposite from the above-described plurality of routing layers 315, for example, to accommodate additional turns of the transformer primary winding P and/or additional transformer secondary windings S or turns thereof. Vias (not shown) extend through component layer 340 to electrically couple turns of the transformer windings formed in routing layers 315 to corresponding winding turns in routing layers 615. FIG. 6 further illustrates three columns 401a, 402a, 403a forming the part of the magnetic core that is embedded in component layer 340, wherein columns 401a, 402a, 403a preferably span a thickness of component layer 340 and are spaced apart from one another to be aligned with the legs of the E-shaped part 500b of the magnetic core and with legs of another E-shaped part 600c of the magnetic core that is bonded to a surface 38 which overlays routing layers 615. According to the illustrated embodiment, columns 401a, 402a, 403a effectively extend the legs of part 600c and complete the magnetic path of the core that encompasses both pluralities of routing layers 315, 615. It should be noted that the same materials and methods referenced above, to form the plurality of routing layers 315, may be employed to form the other plurality of routing layers 615.

FIG. 7 is an exploded schematic illustrating another transformer embodiment, wherein primary and secondary windings P, S are formed in the aforementioned planar helical configuration. The turns of each winding extend around an axis that is approximately parallel to the major plane of routing layers 315, and span across routing layers 315, such that a portion of each turn is formed along two of routing layers 315 and another portion of each turn is formed by vias (not shown) that extend through routing layers 315. FIG. 7 illustrates one or more secondary windings S located within primary winding P, although the opposite arrangement may be employed. The dashed line arrows of FIG. 7 represent the path of magnetic flux for the core that includes parts 400a and 400b.

Figure 8A:
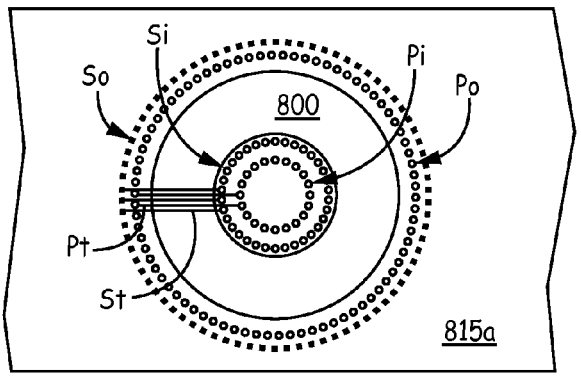
FIGS. 8A-B are a top plan view and an exploded perspective schematic, respectively, of a portion of a partially formed wafer level package, according to yet further embodiments.
Figure 8B:
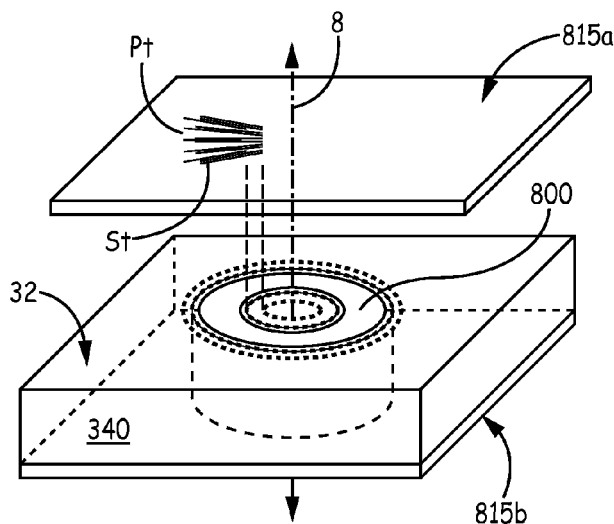
Figure 8C:
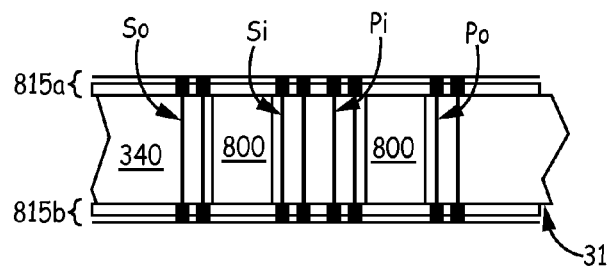
FIG. 8C is a cross-section view of the package shown in FIGS. 8A-B.

FIGS. 8A-B are a top plan view and an exploded perspective schematic, respectively, of a portion of a partially formed wafer level package, according to yet further embodiments; and FIG. 8C is a cross-section view of the package shown in FIGS. 8A-B. FIGS. 8A-C illustrate the package including component layer 340 with the aforementioned opposing sides 31, 32, at least one routing layer 815a overlaying side 32, and at least one routing layer overlaying side 31. FIGS. 8A-C further illustrate a portion of a transformer that includes a toroid-shaped planar magnetic core 800 embedded in component layer 340 and spanning a thickness thereof, for example, ranging from approximately 500 micrometers to approximately 1100 micrometers; primary and secondary windings of the transformer each include inner portions Pi, Si and outer portions Po, So, and top portions Pt, St and bottom portions (not shown). It should be noted that the illustrated transformer may include one secondary winding or a plurality of secondary windings.

According to the illustrated embodiment, the winding inner and outer portions Pi, Si and Po, So extend through a thickness of component layer 340, inside and outside, respectively, a perimeter of magnetic core 800, and approximately parallel with a central axis 8 of core 800; the winding top portions Pt, St extend along routing layer 815*a*, and winding bottom portions extend along routing layer 815*b*, wherein each of the top and bottom portions connect an inner portion to a corresponding outer portion to complete a turn of each winding. For simplicity in illustration, FIGS. 8A-B only show top portions of several turns of the primary and secondary windings. Opposing terminal ends of one or more of the primary and secondary windings may be directly electrically connected with conductive runners of corresponding components that are also embedded in component layer 340, for example, as described above in conjunction with FIG. 3B, or the terminal ends of one or more windings may be formed as bond pads on an outer surface of the package.

With further reference to FIGS. 8A-C, one or both of winding inner portions Pi, Si and outer portions Po, So are formed by isolated conductive vias extending through the component layer. The vias may be formed by drilling holes through the cured polymer mold compound of component layer 340, and then filling each hole with a conductive material, i.e. copper, as an initial step in an RCP process. Subsequent steps of the RCP process build up routing layers 815*a*, 815*b* with conductive traces (top and bottom portions of the windings) that interconnect inner and outer vias to complete each turn of the primary and secondary windings. The number of turns for each winding is a function of via formation, and, according to an exemplary embodiment, when an inner diameter of core 800 is approximately 5,000 micrometers and an outer diameter of core 800 is approximately 10,000 micrometers, and each via diameter is between approximately 100 micrometers and approximately 150 micrometers, with a center-to-center spacing of the vias of between approximately 175 micrometers and approximately 225 micrometers, the transformer includes 3 secondary windings and has a secondary to primary turn ratio of between approximately 20:1 and approximately 30:1. According to some alternate embodiments, for example, to achieve closer spacing of winding inner portions Pi, Si, the winding inner portions are pre-formed together in an insulated array, i.e. embedded in a polymer slug, which is then press fit inside the perimeter of planar toroid-shaped magnetic core 800, either before embedding core 800 in component layer 340, or after embedding core 800 and drilling out an entirety of the cured polymer mold compound that is within the perimeter of embedded core 800. The pre-formed insulated array may be formed by over-molding copper wires with the same polymer compound that forms component layer 340.

In the foregoing detailed description, the invention has been described with reference to specific embodiments. However, it may be appreciated that various modifications and changes can be made without departing from the scope of the invention as set forth in the appended claims.

The invention claimed is:

1. A hybrid integrated circuit formed in a wafer level package for an implantable medical device, the wafer level package comprising a polymer component layer overlaid by a plurality of routing layers, and the integrated circuit comprising:
 a plurality of active devices and passive components embedded in the component layer;
 another passive component including a winding, at least a portion of the winding being formed along one or more of the plurality of routing layers; and
 a plurality of conductive runners extending along the plurality of routing layers, each runner being electrically coupled to a corresponding one or more of the embedded devices and components;
wherein at least one of the conductive runners is electrically coupled to the other passive component and is located on a common routing layer with the winding, wherein:
 the other passive component comprises a transformer such that the winding is a primary winding of the transformer and the transformer further comprises one or more secondary windings, the one or more secondary windings being formed along one or more of the plurality of routing layers;
 the wafer level package further comprises a planar magnetic core of the transformer, the planar magnetic core comprising a first part and a second part;
 the first part of the planar magnetic core is embedded in the component layer; and
 the second part of the core is bonded to a surface of the wafer level package, the surface overlaying the plurality of routing layers, such that the routing layers are sandwiched between the component layer and the second part of the core.

2. The circuit of claim 1, wherein:
the primary winding of the transformer is formed in a planar spiral configuration on at least two layers of the plurality of routing layers; and
each of the one or more secondary windings is formed in the spiral configuration on either of the same at least two layers of the plurality of routing layers, or different layers of the plurality of routing layers from the at least two layers.

3. The circuit of claim 1, wherein the primary winding and the one or more secondary windings of the transformer are formed in a planar helical configuration with turns spanning multiple layers of the plurality of routing layers.

4. The circuit of claim 1, wherein the second part of the magnetic core of the transformer includes three legs spaced apart from one another and extending from the surface and into the plurality of routing layers.

5. The circuit of claim 4, wherein a gap between the three legs of the second part of the magnetic core and the first part of the magnetic core is approximately equal to a thickness of one of the plurality of routing layers.

6. The circuit of claim 4, wherein:
the plurality of routing layers comprises a first plurality and the wafer level package further comprises a second plurality of routing layers overlaying the component layer on a side thereof that is opposite that which is overlaid by the first plurality of routing layers;

the primary and secondary windings of the transformer are further formed along the second plurality of routing layers;

the planar magnetic core of the transformer further comprises a third part;

the first part of the core is divided into three columns spaced apart from one another within the component layer and aligned with the three legs of the second part of the core;

the third part of the core is bonded to an opposite surface of the wafer level package, the opposite surface overlaying the second plurality of routing layers, such that the second plurality of routing layers are sandwiched between the component layer and the third part of the core; and the third part of the core includes legs spaced apart from one another, extending through the second plurality of routing layers, and aligned with the three columns of the first part of the core.

7. The circuit of claim 1, wherein the second part of the magnetic core of the transformer includes three legs spaced apart from one another and extending from the surface, through the plurality of routing layers, and into close proximity with the first part of the magnetic core.

8. The circuit of claim 1, wherein:

the plurality of routing layers comprises a first routing layer overlaying a first side of the component layer and a second routing layer overlaying a second side of the routing layer;

the other passive component comprises a transformer such that the winding is a primary winding of the transformer and the transformer further comprises one or more secondary windings;

the wafer level package further comprises a toroid-shaped planar magnetic core embedded in the component layer;

the primary winding and each of the one or more secondary windings comprise inner and outer portions extending through a thickness of the component layer, inside and outside, respectively, a perimeter of the magnetic core and approximately parallel with a central axis of the core; and the primary winding and each of the one or more secondary windings comprise top and bottom portions extending along the first and second routing layers, respectively, each of the top and bottom portions connecting an inner portion to a corresponding outer portion.

9. The circuit of claim 8, wherein one or both of the inner portions and the outer portions of the primary winding and the one or more secondary windings are formed by isolated conductive vias extending through the component layer.

10. The circuit of claim 8, wherein the inner portions of the primary winding and the one or more secondary windings are pre-formed together in an insulated array that is press-fit inside the perimeter of the magnetic core.

* * * * *